(12) United States Patent
Vogt et al.

(10) Patent No.: US 8,865,777 B2
(45) Date of Patent: Oct. 21, 2014

(54) KIT AND METHOD FOR PRODUCING BONE CEMENT

(75) Inventors: Sebastian Vogt, Erfurt (DE); Hubert Büchner, Nürnberg (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 13/558,579

(22) Filed: Jul. 26, 2012

(65) Prior Publication Data

US 2013/0030058 A1   Jan. 31, 2013

Related U.S. Application Data

(60) Provisional application No. 61/523,557, filed on Aug. 15, 2011.

(30) Foreign Application Priority Data

Jul. 27, 2011   (DE) .......................... 10 2011 108 574

(51) Int. Cl.

| | | |
|---|---|---|
| A61K 6/083 | (2006.01) | |
| A61L 24/04 | (2006.01) | |
| A61L 27/16 | (2006.01) | |
| A61L 27/26 | (2006.01) | |
| A61L 27/50 | (2006.01) | |
| A61L 24/00 | (2006.01) | |
| A61L 24/06 | (2006.01) | |

(52) U.S. Cl.
CPC ............... *A61L 24/043* (2013.01); *A61L 27/16* (2013.01); *A61L 27/26* (2013.01); *A61L 27/50* (2013.01); *A61L 24/001* (2013.01); *A61L 24/06* (2013.01); *A61L 2430/02* (2013.01)
USPC ........................ 514/772.6; 523/116

(58) Field of Classification Search
None
See application file for complete search history.

(56) References Cited

U.S. PATENT DOCUMENTS

| | | | |
|---|---|---|---|
| 4,015,945 | A | 4/1977 | Frankel et al. |
| 4,308,190 | A | 12/1981 | Walkowiak et al. |
| 4,396,476 | A | 8/1983 | Roemer et al. |
| 6,409,972 | B1 | 6/2002 | Chan |
| 6,871,996 | B2 | 3/2005 | Jonsson |
| 7,989,519 | B2 | 8/2011 | Vogt et al. |
| 2009/0105144 | A1 | 4/2009 | Vogt et al. |
| 2009/0105366 | A1 | 4/2009 | Vogt et al. |
| 2010/0159027 | A1 | 6/2010 | Vogt et al. |
| 2010/0273911 | A1 | 10/2010 | Hasenwinkel et al. |
| 2011/0112210 | A1 | 5/2011 | Vogt et al. |
| 2011/0183932 | A1 | 7/2011 | Vogt et al. |
| 2011/0313078 | A1 | 12/2011 | Vogt et al. |

FOREIGN PATENT DOCUMENTS

| | | |
|---|---|---|
| AU | 2011202926 A1 | 1/2012 |
| CN | 1446591 A | 10/2003 |
| CN | 101934097 A | 1/2011 |
| DE | 102007050763 A1 | 4/2009 |
| DE | 10 2007 050 762 B3 | 5/2009 |
| DE | 102008030312 A1 | 1/2010 |
| DE | 102008064657 A1 | 4/2010 |
| DE | 102010005956 A1 | 7/2011 |
| DE | 102010024653 A1 | 12/2011 |
| EP | 0674888 A1 | 10/1995 |
| EP | 0971677 B1 | 2/2005 |
| EP | 1246651 B1 | 3/2009 |
| JP | 2003-181270 A | 7/2003 |
| JP | 2009-101159 A | 5/2009 |
| JP | 2009-101160 A | 5/2009 |
| JP | 2009-102640 A | 5/2009 |
| WO | 9824398 A1 | 6/1998 |
| WO | 2010098305 A1 | 9/2010 |

OTHER PUBLICATIONS

Charnley, "Anchorage of the Femoral Head Prosthesis to the Shaft of the Femur", The Journal of Bone and Joint Surgery, vol. 42 B, No. 1, pp. 28-30 (1960).
Office Action issued Mar. 15, 2012 in DE Application No. 10 2011 108 574.6.
Office Action issued Apr. 12, 2013 in AU Application No. 2012205219.
Rodrigues et al, "Pseudoplasticity and setting properties of two-solution bone cement containing poly(methyl methacrylate) microspheres and nanospheres for kyphoplasty and vertebroplasty," Journal of Biomedical Materials Research, Part B: Applied Biomaterials, vol. 91B, No. 1, pp. 248-256 (2009).
English translation of an Office Action issued Nov. 26, 2013 in JP Application No. 2012-160303.
Office Action issued Feb. 20, 2014 in DE Application No. 10 2011 108 574.6.
Office Action issued Jan. 28, 2014 in CN Application No. 201210263368.8.

*Primary Examiner* — David J Blanchard
*Assistant Examiner* — Daniel F Coughlin
(74) *Attorney, Agent, or Firm* — Panitch Schwarze Belisario & Nadel LLP

(57) ABSTRACT

A kit for producing bone cement includes at least one paste A and one paste B. Paste A contains at least one monomer (a1) for radical polymerization; at least one polymer (a2) insoluble in monomer (a1); at least one polymer (a3) soluble in monomer (a1); and at least one radical polymerization initiator (a4). The weight ratio of the at least one polymer (a2) to the at least one polymer (a3) is at least 2 to 1. Paste B contains at least one monomer (b1) for radical polymerization; at least one polymer (b2) and at least one accelerator (b3) soluble in monomer (b1); and optionally a polymer (b4) insoluble in monomer (b1). The maximum quantity of polymer (b4) is 5% by weight, relative to the total weight of paste B. The weight ratio of polymer (b4) to the at least one polymer (b2) is no more than 0.2.

15 Claims, No Drawings

KIT AND METHOD FOR PRODUCING BONE CEMENT

CROSS-REFERENCE TO RELATED APPLICATIONS

The present application claims the benefit of U.S. Provisional Patent Application No. 61/523,557, filed Aug. 15, 2011, the subject matter of which is hereby incorporated by reference.

BACKGROUND OF THE INVENTION

The present invention relates to a kit for producing bone cement and a method for producing bone cement.

Conventional poly(methylmethacrylate) bone cements (PMMA bone cements) have been known for decades and are based on the ground-breaking work of Sir Charnley (Charnley, J., "Anchorage of the Femoral Head Prosthesis of the Shaft of the Femur, *J. Bone Joint Surg.* 42:28-30 (1960)). The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers that are made by polymerization, preferably suspension polymerization, based on methylmethacrylate and co-monomers, such as styrene, methylacrylate or similar monomers, (ii) a radio-opacifier, and (iii) an initiator, (e.g. dibenzoylperoxide). Mixing the powder component and the monomer component, the polymers of the powder component in the methylmethacrylate swell, which generates a dough that can be shaped plastically. Simultaneously, the activator, N,N-dimethyl-p-toluidine, reacts with dibenzoylperoxide, which disintegrates and forms radicals in the process. The radicals thus formed trigger the radical polymerization of the methylmethacrylate. Upon advancing polymerization of the methylmethacrylate, the viscosity of the cement dough increases until the cement dough solidifies and thus is cured.

The underlying mechanical requirements of PMMA bone cements, such as 4-point flexural strength, flexural modulus, and compressive strength, are described in ISO 5833. The property of PMMA bone cement to be non-tacky is of essential importance to users of PMMA bone cements. The term "non-tackiness" is defined in ISO 5833 and indicates that the PMMA bone cement has reached the processing phase in the monomer after mixing of the components owing to swelling of the polymers present in the cement powder. A PMMA bone cement must be non-tacky as a matter of principle in order for the user to be able to shape and apply the cement. The PMMA bone cement must not stick to the gloves and application aids, such as mixing systems, crucibles or spatulas.

The essential disadvantage of the previous PMMA bone cements for the medical user is that the user needs to mix the liquid monomer component and the powder component in a mixing system or in crucibles right before applying the cement. Mixing errors can easily occur in the process and adversely affect the quality of the cement. Moreover, the components must be mixed rapidly. In this context, it is important to mix all of the cement powder and monomer component without forming lumps and prevent the introduction of air bubbles during the mixing process. Unlike manual mixing, the use of vacuum mixing systems prevents the formation of air bubbles in the cement dough to a large extent. Examples of mixing systems are disclosed in U.S. Pat. No. 4,015,945, European patent application publication EP 0674888 A1, and Japanese patent application publication (Kokai) JP 2003181270A. However, vacuum mixing systems necessitate an additional vacuum pump and are therefore relatively expensive. Moreover, depending on the type of cement concerned, a certain waiting time is required after mixing the monomer component and the powder component until the cement dough is tack-free and can be applied. Because of the large variety of errors that can occur while mixing conventional PMMA bone cements, appropriately trained personnel are required for this purpose. The corresponding training is associated with considerable expenses. Moreover, mixing of the liquid monomer component and the powder component is associated with exposure of the user to monomer vapors and particles released from the powder-like cement. Another essential disadvantage of conventional PMMA bone cements is that both the powder component and the monomer component each need to be manufactured in a doubly sterile-packaged manner, which requires at least four sterile packaging means for each package of bone cement.

German Patent DE 10 2007 050 762 B3 proposes a bone cement comprising two pastes as an alternative to conventional powder-liquid polymethylmethacrylate bone cements. These pastes each contain a methacrylate monomer for radical polymerization, a polymer soluble in the methacrylate monomer, and a particulate polymer insoluble in the methacrylate monomer. In addition, one of the pastes contains a radical polymerization initiator, whereas the other paste comprises a polymerization activator. As a result of the selected composition, the bone cement produced from the pastes possesses sufficiently high viscosity and cohesion in order to withstand the pressure from bleeding until it is fully cured. When the two pastes are mixed, the polymerization initiator reacts with the accelerator to form radicals that initiate the radical polymerization of the methacrylate monomers. Owing to the advancing polymerization, the paste is cured while the methacrylate monomers are consumed. It has been found that, even if highly cross-linked poly(methacrylate) particles are used as particulate polymer insoluble in the methacrylate monomer, these take up and enclose small fractions of methacrylate monomer and compounds dissolved therein. This causes the insoluble polymer particles of the one paste to contain inclusions of monomer liquid and initiator dissolved therein, whereas the insoluble polymer particles of the other paste in turn contain inclusions of monomer liquid and accelerator dissolved therein. After the two pastes are mixed, the phase consisting of the methacrylate monomer and the polymer dissolved therein, in which the insoluble polymer particles are suspended, cures while forming bone cement that is ready for application. Afterwards, the initially enclosed monomer liquid diffuses from the insoluble polymer particles and undergoes secondary polymerization. The monomer liquid diffusing from the insoluble polymer particles acts as a plasticizer, due to the secondary polymerization, until it is consumed. This leads to the initially cured bone cement pastes meeting the requirements of ISO 5833, but also still showing pronounced secondary curing due to secondary polymerization of the monomer liquid diffusing from the insoluble polymer particles.

BRIEF SUMMARY OF THE INVENTION

It is therefore an object of the invention to provide a kit for producing bone cement that possesses high initial strength and shows only little secondary curing. Moreover, another object of the invention is to provide a method for producing a bone cement of this type.

The invention therefore provides a kit for producing bone cement, the kit comprising at least a paste A and a paste B, wherein:
  (a) paste A contains;
    at least one monomer (a1) for radical polymerization;
    at least one polymer (a2) insoluble in monomer (a1);
    at least one polymer (a3) soluble in monomer (a1); and
    at least one radical polymerization initiator (a4);
  wherein the weight ratio of the at least one polymer (a2) insoluble in monomer (a1) to the at least one polymer (a3) soluble in monomer (a1) is at least 2 to 1; and
  (b) paste B contains:
    at least one monomer (b1) for radical polymerization;
    at least one polymer (b2) soluble in monomer (b1); and
    at least one accelerator (b3) soluble in monomer (b1),
    optionally a polymer (b4) insoluble in monomer (b1),
  wherein the maximum quantity of polymer (b4) insoluble in monomer (b1) is 5% by weight, relative to the total weight of paste B; and
  wherein the weight ratio of polymer (b4) insoluble in monomer (b1) to the at least one polymer (b2) soluble in monomer (b1) is no more than 0.2.

Moreover, the invention provides a method for producing bone cement, in which
  (i) a kit is provided for producing bone cement, the kit comprising at least a paste A and a paste B, wherein:
    (a) paste A contains:
      at least one monomer (a1) for radical polymerization;
      at least one polymer (a2) insoluble in monomer (a1);
      at least one polymer (a3) soluble in monomer (a1); and
      at least one radical polymerization initiator (a4);
    wherein the weight ratio of the at least one polymer (a2) insoluble in monomer (a1) to the at least one polymer (a3) soluble in monomer (a1) is at least 2 to 1; and
    (b) paste B contains:
      at least one monomer (b1) for radical polymerization;
      at least one polymer (b2) soluble in monomer (b1); and
      at least one accelerator (b3) soluble in monomer (b1),
      optionally a polymer (b4) insoluble in monomer (b1),
    wherein the maximum quantity of polymer (b4) insoluble in monomer (b1) is 5% by weight, relative to the total weight of paste B; and
    wherein the weight ratio of polymer (b4) insoluble in monomer (b1) to the at least one polymer (b2) soluble in monomer (b1) is no more than 0.2: and
  (ii) pastes A and B are mixed with each other.

DETAILED DESCRIPTION OF THE INVENTION

The kit according to the invention for producing bone cement therefore has an asymmetrical structure with respect to the qualitative and quantitative composition. A first paste comprises a monomer for radical polymerization, a polymer insoluble in the monomer, and a polymer soluble in the monomer. Moreover, the first paste also contains a polymerization initiator. The first paste comprises a high fraction of the polymer insoluble in the monomer. A second paste comprises a monomer for radical polymerization, a polymer soluble in the monomer, and an accelerator. The second paste comprises no polymer insoluble in the monomer or just a small fraction of polymer insoluble in the monomer.

This asymmetrical structure results in a special technical effect: Due to the presence of the polymerization initiator in the first paste, which contains large quantities of insoluble polymer, the insoluble polymer can enclose the monomer for radical polymerization along with the polymerization initiator dissolved therein. In contrast, inclusion of the accelerator in insoluble polymer is basically impossible, since the accelerator is present in the second paste only and since the second paste contains no or only small quantities of the insoluble polymer. After mixing the two pastes, the polymerization therefore commences within a phase that comprises the monomer for radical polymerization, the polymer dissolved therein, the polymerization initiator, and the accelerator. Since the accelerator is provided only in the second paste, which is absolutely or largely free of insoluble polymer, the entire quantity of accelerator is distributed homogeneously in the mixture of the two pastes. Secondary diffusion of monomer for radical polymerization and accelerator is basically excluded, since no or nearly no insoluble polymer is available for enclosing the monomer for radical polymerization and the accelerator. As a result, only monomer for radical polymerization including polymerization initiator dissolved therein can exit from the insoluble polymer present in the mixture of the two pastes. In this case, the monomer for radical polymerization is polymerized, directly assisted by the accelerator present in the surrounding matrix. Moreover, the accelerator can diffuse into the particles of insoluble polymer and polymerize the residues of monomer for radical polymerization enclosed therein in the presence of the polymerization initiator that is also present. Therefore, the present invention largely excludes not yet polymerized monomer from exiting from the particles of the insoluble polymer. Accordingly, the monomer for radical polymerization is not available as plasticizer, which allows the secondary curing of the bone cement to be reduced markedly.

The present invention provides a kit for producing bone cement. According to the invention, a kit shall be understood to be a system made up of at least two components. Although reference to two components is made in the following, the kit can just as well contain more than two components, for example three, four, five or more than five components, if applicable. The individual components preferably are provided to be packaged separate from each other, such that the ingredients of the one kit component do not contact the ingredients of another kit component. Accordingly, it is feasible, for example, to package the respective kit components separate from each other and to store them together in a reservoir container.

According to a preferred embodiment, the kit is implemented through a device for producing bone cement. A device of this type for producing bone cement can comprise, for example, at least two containers, wherein a first container contains paste A and a second container contains paste B. At least one of the two containers can preferably be opened by a user in order to allow pastes A and B to be mixed after opening the container. Moreover, the device for producing bone cement is preferably designed such that, after opening at least one of the two containers, the pastes present in the two containers can contact each other. Aside from the two containers, the device for producing bone cement can, in particular, also contain a mixing unit for mixing pastes A and B to form a mixed product. The device for producing bone cement can, for example, be implemented through a double cartridge in which pastes A and B are provided separately from each other. If applicable, a mixing unit, like a static or actively-driven mixer, can be arranged on the double cartridge in order to attain the mixing of pastes A and B.

According to the invention, the kit comprises at least one paste A and one paste B.

Paste A contains at least one monomer (a1) for radical polymerization. The at least one monomer (a1) for radical polymerization preferably has a pH in water in the range of 5-9.

Preferably, the monomer (a1) for radical polymerization is liquid at a temperature of 25° C. and a pressure of 1013 hPa. According to a preferred embodiment, the monomer (a1) for radical polymerization can be distilled.

The monomer (a1) for radical polymerization preferably is a methacrylic acid ester. Preferably, the methacrylic acid ester is a monofunctional, difunctional or trifunctional methacrylic acid ester.

The methacrylic acid ester preferably is an aliphatic methacrylic acid ester and, more preferably, is a methacrylic acid alkylester. According to a preferred embodiment, the methacrylic acid alkylesters are esters of methacrylic acid and alcohols comprising 1-20 carbon atoms, more preferably 1-10 carbon atoms, even more preferably 1-6 carbon atoms, and particularly preferably 1-4 carbon atoms. The alcohols can be substituted or non-substituted and preferably are non-substituted. Moreover, the alcohols can be saturated or unsaturated and preferably are saturated. The alcohols can be monoalcohols, dialcohols or polyalcohols.

According to another preferred embodiment, the methacrylic acid ester can be a compound represented by the following formula:

$CH_2=C(CH_3)C(O)(CH_2CH_2)_nOC(O)C(CH_3)=CH_2$, wherein n is an integer. Preferably, n is an integer in the range of 1-10, more preferably an integer in the range of 1-4, and even more preferably is 1 or 2.

According to a particularly preferred embodiment, the monomer (a1) for radical polymerization is selected from the group consisting of methacrylic acid methylester, methacrylic acid ethylester, ethyleneglycol dimethacrylate, and butane-1,4-dioldimethacrylate.

The monomer (a1) for radical polymerization used according to the invention preferably has a molar mass of less than 1,000 g/mol. This also comprises monomers for radical polymerization that are components of a mixture of monomers, wherein at least one of the monomers for radical polymerization of the mixture of monomers has a defined structure having a molar mass of less than 1,000 g/mol.

Paste A preferably contains 15-75% by weight, more preferably 15-70% by weight, even more preferably 20-60% by weight, and particularly preferably 25-50% by weight of at least one monomer (a1) for radical polymerization, relative to the total weight of paste A.

Moreover, paste A contains at least one polymer (a2) insoluble in monomer (a1). Preferably, the polymer (a2) insoluble in monomer (a1) is particulate. According to a particularly preferred embodiment, the polymer (a2) insoluble in monomer (a1) has an average particle size in the range of 10 nm-500 μm and particularly preferably in the range of 100 nm-500 μm. The average particle size shall be understood herein to mean a size range that applies to at least 90 percent of the particles.

The polymer (a2) insoluble in monomer (a1) preferably has a mean (by weight) molar mass of at least 150,000 g/mol and more preferably a mean (by weight) molar mass of at least 500,000 g/mol. The specification of the molar mass refers to the molar mass determined by viscometry.

The polymer (a2) insoluble in monomer (a1) can be either cross-linked or non-cross-linked, and preferably is cross-linked. In this context, the cross-linking is effected through a difunctional compound. The difunctional compound can be selected, for example, from the group consisting of alkyleneglycol dimethacrylates. An expedient cross-linker is, for example, ethyleneglycol dimethacrylate.

The polymer (a2) insoluble in monomer (a1) can be a homopolymer or a copolymer. Preferably, the polymer (a2) insoluble in monomer (a1) is a polymer of a methacrylic acid ester. According to a preferred embodiment, the polymer (a2) insoluble in monomer (a1) is a homopolymer or a copolymer of a methacrylic acid alkylester. According to a particularly preferred embodiment, the at least one polymer (a2) insoluble in monomer (a1) is selected from the group consisting of cross-linked poly(methylmethacrylate-co-methacrylate) and cross-linked poly(methylmethacrylate).

The polymer (a2) is insoluble in the at least one monomer (a1) for radical polymerization. According to the invention, the polymer (a2) is insoluble in the monomer (a1) for radical polymerization, if the solubility of the polymer (a2) in the monomer (a1) for radical polymerization at a temperature of 25° C. is less than 50 g/l, preferably is less than 25 g/l, more preferably is less than 10 g/l, and even more preferably is less than 5 g/l.

The fraction of the at least one polymer (a2) insoluble in monomer (a1) preferably is in the range of 20-70% by weight, more preferably is in the range of 25-60% by weight, even more preferably is in the range of 30-55% by weight, and particularly preferably is in the range of 34-47% by weight, relative to the total weight of paste A.

Moreover, paste A contains at least one polymer (a3) soluble in monomer (a1). The polymer (a3) soluble in monomer (a1) preferably is a polymer having a mean (by weight) molar mass of less than 500,000 g/mol and more preferably is a polymer having a mean (by weight) molar mass of less than 150,000 g/mol. The specification of the molar mass refers to the molar mass determined by viscometry.

The polymer (a3) insoluble in monomer (a1) can be either cross-linked or non-cross-linked, and preferably is cross-linked.

The polymer (a3) soluble in monomer (a1) can be a homopolymer or a copolymer.

Preferably, the at least one polymer (a3) soluble in the monomer (a1) for radical polymerization is a polymer of a methacrylic acid ester. According to a particularly preferred embodiment, the at least one polymer (a3) soluble in the monomer (a1) for radical polymerization is a copolymer of methacrylic acid methylester.

According to another particularly preferred embodiment, the at least one polymer (a3) soluble in monomer (a1) is selected from the group consisting of poly(methacrylic acid methylester) (PMMA), poly(methacrylic acid ethylester) (PMAE), poly(methacrylic acid propylester) (PMAP), poly(methacrylic acid isopropylester), poly(methylmethacrylate-co-methylacrylate), and poly(styrene-co-methylmethacrylate).

The polymer (a3) is soluble in the at least one monomer (a1) for radical polymerization. According to the invention, the polymer (a3) is soluble in the at least one monomer (a1) for radical polymerization, if the solubility of the polymer (a3) in the monomer (a1) for radical polymerization at a temperature of 25° C. is at least 25 g/l, more preferably is at least 50 g/l, and particularly preferably is at least 100 g/l.

The fraction of the polymer (a3) soluble in monomer (a1) preferably is in the range of 1-25% by weight, more preferably is in the range of 2-20% by weight, even more preferably is in the range of 2-18% by weight, and particularly preferably is in the range of 3-16% by weight, relative to the total weight of paste A.

The weight ratio of the at least one polymer (a2) insoluble in monomer (a1) to the at least one polymer (a3) soluble in monomer (a1) in paste A is at least 2 to 1. According to a preferred embodiment, the weight ratio of the at least one polymer (a2) insoluble in monomer (a1) to the at least one polymer (a3) soluble in monomer (a1) in paste A is at least 2.1 to 1.0, more preferably at least 2.2 to 1.0, and even more preferably at least 2.3 to 1.0.

Paste A contains a radical polymerization initiator (a4). Preferably, the radical polymerization initiator (a4) is soluble in the at least one monomer (a1) for radical polymerization. According to the invention, the radical polymerization initiator (a4) is soluble in the at least one monomer (a1) for radical polymerization, if the solubility of the radical polymerization initiator (a4) in the monomer (a1) for radical polymerization at a temperature of 25° C. is at least 25 g/l, more preferably at least 50 g/l, and particularly preferably at least 100 g/l.

It can be advantageous to use as radical polymerization initiator (a4) a compound that can decompose to form radicals both in accelerator-induced manner and upon thermal stress.

According to a particularly preferred embodiment, the radical polymerization initiator (a4) is a peroxide. The term "peroxide" refers to compounds containing at least one peroxy group (—O—O—). Suitable polymerization initiators for polymerization of monomers for radical polymerization are known to the person skilled in the art. For example, dibenzoylperoxide and cumenehydroperoxide have proven to be suitable peroxides.

According to a further preferred embodiment, the radical polymerization initiator (a4) is a barbituric acid derivative. The barbituric acid derivative can be selected, for example, from the group consisting of 1,5-disubstituted barbiturates, 1,3,5-trisubstituted barbiturates, and 1,3,5-tetrasubstituted barbiturates. In this context, there is no specific limitation with regard to the type of substituents on the barbituric acid. The substituents can be, for example, aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred. Barbiturates having one substituent each at position 1 and position 5, one substituent each at positions 1, 3, and 5 or one substituent each at positions 1 and 3 and two substituents at position 5 are used preferably. According to a preferred embodiment, the barbituric acid derivative is a 1,5-disubstituted barbiturate or a 1,3,5-trisubstituted barbiturate, for example a 1,5-dialkylbarbiturate, a 1-cycloalkyl-5-alkylbarbiturate or a 1-aryl-5-alkylbarbiturate. 1,3,5-tetrasubstituted barbiturates can also be used, although they are capable of crossing the blood-brain barrier and thus possess pharmacological activity. According to a particularly preferred embodiment, the barbituric acid derivative is selected from the group consisting of 1-cyclohexyl-5-ethylbarbituric acid, 1-phenyl-5-ethylbarbituric acid, 1-benzyl-5-ethylbarbituric acid, and 1,3,5-trimethylbarbituric acid.

The fraction of the at least one radical polymerization initiator (a4) preferably is in the range of 0.00001-15% by weight, more preferably in the range of 0.001-10% by weight, even more preferably in the range of 0.01-10% by weight, and particularly preferably in the range of 0.1-10% by weight, relative to the total weight of paste A.

Paste B contains at least one monomer (b1) for radical polymerization. The at least one monomer (b1) for radical polymerization preferably has a pH in water in the range of 5-9. Preferably, the monomer (b1) for radical polymerization is liquid at a temperature of 25° C. and a pressure of 1013 hPa. According to a preferred embodiment, the monomer (b1) for radical polymerization can be distilled.

The monomer (b1) for radical polymerization preferably is a methacrylic acid ester. Preferably, the methacrylic acid ester is a monofunctional, difunctional or trifunctional methacrylic acid ester.

The methacrylic acid ester preferably is an aliphatic methacrylic acid ester and, more preferably is a methacrylic acid alkylester. According to a preferred embodiment, the methacrylic acid alkylesters are esters of methacrylic acid and alcohols comprising 1-20 carbon atoms, more preferably 1-10 carbon atoms, even more preferably 1-6 carbon atoms, and particularly preferably 1-4 carbon atoms. The alcohols can be substituted or non-substituted and preferably are non-substituted. Moreover, the alcohols can be saturated or unsaturated and preferably are saturated. The alcohols can be monoalcohols, dialcohols or polyalcohols.

According to another preferred embodiment, the methacrylic acid ester can be a compound represented by the following formula:

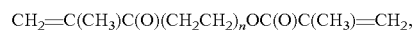

wherein n is an integer. Preferably, n is an integer in the range of 1-10, more preferably an integer in the range of 1-4, and even more preferably is 1 or 2.

According to a particularly preferred embodiment, the monomer (b1) for radical polymerization is selected from the group consisting of methacrylic acid methylester, methacrylic acid ethylester, ethyleneglycol dimethacrylate, and butane-1,4-dioldimethacrylate.

The monomer (b1) for radical polymerization used according to the invention preferably has a molar mass of less than 1,000 g/mol. This also comprises monomers for radical polymerization that are components of a mixture of monomers, wherein at least one of the monomers for radical polymerization of the mixture of monomers has a defined structure having a molar mass of less than 1,000 g/mol.

Paste B preferably contains 10-70% by weight, more preferably 15-60% by weight, even more preferably 20-55% by weight, and particularly preferably 25-50% by weight of at least one monomer (b1) for radical polymerization, relative to the total weight of paste B.

Moreover, paste B contains at least one polymer (b2) soluble in monomer (b1). The polymer (b2) soluble in monomer (b1) preferably is a polymer having a mean (by weight) molar mass of less than 500,000 g/mol and more preferably is a polymer having a mean (by weight) molar mass of less than 150,000 g/mol. The specification of the molar mass refers to the molar mass determined by viscometry.

The polymer (b2) insoluble in monomer (b1) can be either cross-linked or non-cross-linked, and preferably is non-cross-linked.

The polymer (b2) soluble in monomer (b1) can be a homopolymer or a copolymer.

Preferably, the at least one polymer (b2) soluble in the monomer (b1) for radical polymerization is a polymer of a methacrylic acid ester. According to a particularly preferred embodiment, the at least one polymer (b2) soluble in the monomer (b1) for radical polymerization is a copolymer of methacrylic acid methylester.

According to another particularly preferred embodiment, the at least one polymer (b2) soluble in monomer (b1) is selected from the group consisting of poly(methacrylic acid methylester) (PMMA), poly(methacrylic acid ethylester) (PMAE), poly(methacrylic acid propylester) (PMAP), poly(methacrylic acid isopropylester), poly(methylmethacrylate-co-methylacrylate), and poly(styrene-co-methylmethacrylate).

The polymer (b2) is soluble in the at least one monomer (b1) for radical polymerization. According to the invention, the polymer (b2) is soluble in the at least one monomer (b1) for radical polymerization, if the solubility of the polymer (b2) in the monomer (b1) for radical polymerization at a temperature of 25° C. is at least 25 g/l, more preferably at least 50 g/l, and particularly preferably at least 100 g/l.

The fraction of the polymer (b2) soluble in monomer (b1) preferably is in the range of 25-85% by weight, more preferably is in the range of 35-85% by weight, even more preferably is in the range of 40-80% by weight, and particularly preferably is in the range of 50-75% by weight, relative to the total weight of paste B.

In addition, paste B contains at least one accelerator (b3). The accelerator (b3) can be any of the common accelerators in this field.

According to one embodiment, the accelerator (b3) is selected from the group consisting of N,N-dimethyl-p-toluidine, N,N-bis-hydroxyethyl-p-toluidine, N,N-dimethylaniline, 4-N,N-dimethylamino-pyridine, saccharin, lithium chloride, trioctylmethylammoniumchloride, and mixtures thereof. An accelerator (b3) of this type is preferably used when a peroxide is used as polymerization initiator (a4) in paste A of the kit.

According to another embodiment, the accelerator (b3) is an organic copper (II) salt. In this case, the accelerator (b3) is selected from the group consisting of copper(II)-2-ethylhexanoate, copper(II)-methacrylate, copper(II)-acetylacetonate, basic copper(II)-carbonate, and copper(II)-hydroxide. An accelerator (b3) of this type is preferably used when a barbituric acid derivative is used as polymerization initiator (a4) in paste A of the kit. In this case, it can also be advantageous for at least one of the pastes A and B, preferably paste B, to contain a halide salt. The halide salt can be, for example, an inorganic or organic salt of chlorine or bromine. The use of quarternary alkyl, aryl, aryldialkyl, diarylalkyl, or cycloalkyldialkylammonium salts, for example trioctylmethylammonium chloride, has proven to be particularly advantageous. However, hydrohalides or metallohalides can be used just as well.

The fraction of the at least one accelerator (b3) preferably is in the range of 0.00001-15% by weight, more preferably in the range of 0.001-10% by weight, even more preferably in the range of 0.01-10% by weight, and particularly preferably in the range of 0.1-10% by weight, relative to the total weight of paste B.

Optionally, paste B contains a polymer (b4) insoluble in monomer (b1). The maximum content of polymer (b4) insoluble in monomer (b1) in paste B is 5% by weight, relative to the total weight of paste B. Accordingly, paste B can contain no polymer (b4) insoluble in monomer (b1). However, it is possible just as well that paste B contains small quantities of polymer (b4) insoluble in monomer (b1) as long as the content of polymer (b4) insoluble in monomer (b1) does not exceed 5% by weight, relative to the total weight of paste B. According to a preferred embodiment, the maximum content of polymer (b4) insoluble in monomer (b1) is 5% by weight, more preferably 4% by weight, even more preferably 3% by weight, particularly preferably 2% by weight, and even more particularly preferably 1% by weight, relative to the total weight of paste B. However, according to a particularly preferred embodiment, the content of polymer (b4) insoluble in monomer (b1) is 0% by weight, relative to the total weight of paste B.

The weight ratio of polymer (b4) insoluble in monomer (b1) to the at least one polymer (b2) soluble in monomer (b1) is no more than 0.2. Preferably, the weight ratio of polymer (b4) insoluble in monomer (b1) to the at least one polymer (b2) soluble in monomer (b1) is no more than 0.15, more preferably no more than 0.1, even more preferably no more than 0.05, particularly preferably no more than 0.02, and even more particularly preferably equal to 0.

The polymer (b4) insoluble in monomer (b1) can be particulate. It can have an average particle size in the range of 10 nm-500 μm or in the range of 100 nm-500 μm. The average particle size shall be understood herein to mean a size range that applies to at least 90 percent of the particles.

The polymer (b4) insoluble in monomer (b1) can have a mean (by weight) molar mass of at least 150,000 g/mol or of at least 500,000 g/mol. The specification of the molar mass refers to the molar mass determined by viscometry.

The polymer (b4) insoluble in monomer (b1) can be cross-linked or non-cross-linked. In this context, the cross-linking can be effected through a difunctional compound. The difunctional compound can be selected, for example, from the group consisting of alkyleneglycol dimethacrylates. Therefore, a conceivable cross-linker in this context is, for example, ethyleneglycol dimethacrylate.

The polymer (b4) insoluble in monomer (b1) can be a homopolymer or a copolymer.

The polymer (b4) insoluble in monomer (b1) can be a polymer of a methacrylic acid ester. The polymer (b4) insoluble in monomer (b1) can be, for example, a homopolymer or copolymer of a methacrylic acid alkylester.

The at least one polymer (b4) insoluble in monomer (b1) can be selected from the group consisting of cross-linked poly(methylmethacrylate-co-methacrylate) and cross-linked poly(methylmethacrylate).

The polymer (b4) is insoluble in the at least one monomer (b1) for radical polymerization. According to the invention, the polymer (b4) is insoluble in the at least one monomer (b1) for radical polymerization, if the solubility of the polymer (b4) in the monomer (b1) for radical polymerization at a temperature of 25° C. is less than 50 g/l, preferably is less than 25 g/l, more preferably is less than 10 g/l, and even more preferably is less than 5 g/l.

Pastes A and B can contain further components aside from the components explained above. The further components can be present either in paste A, in paste B or in pastes A and B.

According to a preferred embodiment, at least one radio-opacifier is present in at least one of the pastes A and B. The radio-opacifier can be a common radio-opacifier in this field. Suitable radio-opacifiers can be soluble or insoluble in the monomer (a1) for radical polymerization or the monomer (b1) for radical polymerization. The radio-opacifier is preferably selected from the group consisting of metal oxides (for example zirconium oxide), barium sulfate, toxicologically acceptable heavy metal particles (for example tantalum), ferrite, magnetite (optionally even supramagnetic magnetite), and biocompatible calcium salts. The radio-opacifiers preferably have a mean particle diameter in the range of 10 nm-500 μm. Moreover, conceivable radio-opacifiers also include esters of 3,5-bis(acetamido)-2,4,6-triiodobenzoic acid, gadolinium compounds, such as gadolinium chelate involving the esters of 1,4,7,10-tetraazacyclododecane-1,4,7,10-tetraacetic acid (DOTA).

According to another preferred embodiment, at least one of the pastes A and B contains at least one colorant. The colorant can be a common colorant in this field and preferably can be a food colorant. Moreover, the colorant can be soluble or insoluble in the at least one monomer (a1) for radical polymerization or the at least one monomer (b1) for radical polymerization. According to a particularly preferred embodiment, the colorant is selected from the group consisting of E101, E104, E132, E141 (chlorophyllin), E142, riboflavin, and lissamine green. According to the invention, the term "colorant" shall also include color varnishes, for example color varnish green, the aluminum salt of a mixture of E104 and E132.

According to another preferred embodiment, at least one of the pastes A and B contains at least one pharmaceutical agent. The at least one pharmaceutical agent can be present in at least one of pastes A and B in dissolved or suspended form. The pharmaceutical agent can preferably be selected from the group consisting of antibiotics, antiphlogistic agents, steroids, hormones, growth factors, bisphosphonates, cytostatic agents, and gene vectors.

According to a particularly preferred embodiment, the at least one pharmaceutical agent is an antibiotic. Preferably, the at least one antibiotic is selected from the group consisting of aminoglyoside antibiotics, glycopeptide antibiotics, lincosamide antibiotics, gyrase inhibitors, carbapenems, cyclic lipopeptides, glycylcyclines, oxazolidones, and polypeptide antibiotics.

According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, timidazole, omidazole, and colistin, as well as salts and esters thereof. Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somatotropin, testosterone, and estrogen.

Preferably, the at least one growth factor is selected from the group consisting of Fibroblast Growth Factor (FGF), Transforming Growth Factor (TGF), Platelet Derived Growth Factor (PDGF), Epidermal Growth Factor (EGF), Vascular Endothelial Growth Factor (VEGF), insulin-like growth factors (IGF), Hepatocyte Growth Factor (HGF), Bone Morphogenetic Protein (BMP), interleukin-1B, interleukin 8, and nerve growth factor.

The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

According to another preferred embodiment, at least one of the pastes A and B contains at least one biocompatible elastomer. Preferably, the biocompatible elastomer is particulate. Preferably, the biocompatible elastomer is soluble in the at least one monomer (a1) for radical polymerization or the at least one monomer (b1) for radical polymerization. The use of butadiene as biocompatible elastomer has proven to be particularly well-suited.

According to another preferred embodiment, at least one of the pastes A and B contains at least one monomer having adsorption groups. An amide group, for example, can be an adsorption group. Accordingly, the monomer having an adsorption group can be, for example, methacrylic acid amide. Using at least one monomer having adsorption groups would allow the binding of the bone cement to articular endoprostheses to be influenced in a targeted manner.

According to another preferred embodiment, at least one of the pastes A and B contains at least one stabilizer. The stabilizer should be suitable to prevent spontaneous polymerization of the monomers for polymerization that are present in pastes A and B. Moreover, the stabilizer should not undergo interfering interactions with the other components contained in the pastes. Stabilizers of this type are known according to the prior art. According to a preferred embodiment, the stabilizer is 2,6-di-tert-butyl-4-methylphenol and/or 2,6-di-tert-butyl-phenol.

Preferably, the fraction of paste A and the fraction of paste B in the kit according to the invention is 30-70% by weight and 30-70% by weight, respectively, relative to the total weight of pastes A and B.

According to the invention, the purpose of the kit containing at least pastes A and B is the production of bone cement. For this purpose, the at least two pastes A and B are mixed with each other, whereupon a bone cement paste is obtained. Preferably, the mixing ratio is 0.5-1.5 parts by weight of paste A to 0.5-1.5 parts by weight of paste B.

Mixing can be effected with common mixing devices, for example a static mixer or a dynamic mixer. Mixing can be effected in a vacuum or without a vacuum. According to a particularly preferred embodiment, pastes A and B are mixed using the device for producing bone cement explained above. Accordingly, pastes A and B are provided separate from each other in two containers, for example in a double cartridge. By opening at least one of the containers, and preferably of both containers, pastes A and B present in the two containers can contact each other. Pastes A and B can then be mixed by actuating a mixing unit, for example a static or actively driven mixer that is present inside the device.

Ultimately, the bone cement paste can be dispensed from the device for the purpose of application. The application of the bone cement paste preferably proceeds by an application unit facilitating the bone cement paste to be squeezed out.

The bone cement paste that is ultimately obtained after mixing pastes A and B of the kit is tack-free according to the ISO 5833 standard and can be processed instantaneously.

The bone cement generated by curing from the bone cement paste attains high strength within a few minutes after the pastes present in the kit are mixed.

According to a preferred embodiment, the kit according to the invention can be used for mechanical fixation of articular endoprostheses, for covering skull defects, for filling bone cavities, for femuroplasty, for vertebroplasty, for kyphoplasty, for the manufacture of spacers, and for the production of carrier materials for local antibiotics therapy. In this context, the term "spacer" shall be understood to mean implants that can be used temporarily in the scope of the two-step exchange of prostheses in septic revision surgeries.

Carrier materials for local antibiotics therapy can be provided as spheres or sphere-like bodies or as bean-shaped bodies. Besides, it is also feasible to produce rod-shaped or disc-shaped carrier materials that contain the bone cement made from the kit according to the invention. Moreover, the carrier materials can also be threaded onto absorbable or non-absorbable suture material, preferably in a bead-like manner.

The uses according to the invention of bone cement described above are known from the literature and have been described therein on numerous occasions.

According to the invention, the kit is used for the above-described uses in that the pastes contained in the kit are preferably mixed with each other to produce a bone cement paste, which is then used in the above-described uses just in the same manner as pastes known from the prior art.

EXAMPLES

The invention shall be illustrated through the examples described in the following, but without limiting the scope of the invention.

Examples 1-7 and Reference Example 1

For Examples 1-7 and Reference Example 1, pastes A and B were produced to have the compositions specified in the following Tables 1-4.

TABLE 1

Composition of paste A in Examples 1-7.

| | Composition of paste A | | | | | | |
|---|---|---|---|---|---|---|---|
| Example no. | Monomer for radical polymerization (a1) | | | Insoluble polymer (a2) | Soluble polymer (a3) | Polymerization initiator 1 (a4) | Stabilizer |
| | MMA | MA | EGDMA | | | | |
| 1 | 20.2 g | — | 0.6 g | 15.5 g | 6.2 g | 2.0 g | 20 mg |
| 2 | 20.2 g | — | 0.6 g | 15.5 g | 6.2 g | 2.0 g | 20 mg |
| 3 | 20.2 g | — | 0.6 g | 15.5 g | 6.2 g | 2.0 g | 20 mg |
| 4 | 20.2 g | — | 0.6 g | 15.5 g | 6.2 g | 2.0 g | 20 mg |
| 5 | 20.2 g | — | 0.6 g | 15.5 g | 6.2 g | 2.0 g | 20 mg |
| 6 | 20.2 g | — | 0.6 g | 15.5 g | 6.2 g | 2.0 g | 20 mg |
| 7 | 20.2 g | — | 0.6 g | 15.5 g | 6.2 g | 1.5 g | 20 mg |

TABLE 2

Composition of paste B in Examples 1-7.

| | Composition of paste B | | | | | | | |
|---|---|---|---|---|---|---|---|---|
| Example no. | Monomer for radical polymerization (b1) | | | Soluble polymer (b2) | Accelerator 1 (b3) | Colorant | Antibiotic | Stabilizer |
| | MMA | MA | EGDMA | | | | | |
| 1 | 20.2 g | — | — | 16.9 g | 0.4 g | — | — | 35 mg |
| 2 | 20.2 g | — | — | 16.9 g | 0.4 g | — | 3.28 g | 35 mg |
| 3 | 20.2 g | — | — | 16.9 g | 0.4 g | — | 2.19 g | 35 mg |
| 4 | 20.2 g | — | — | 16.9 g | 0.4 g | 50 mg | — | 35 mg |
| 5 | 20.2 g | — | — | 16.9 g | 0.4 g | 50 mg | 2.19 g | 35 mg |
| 6 | 20.2 g | — | — | 16.9 g | 0.4 g | 50 mg | 3.28 g | 35 mg |
| 7 | 20.2 g | — | — | 16.9 g | 0.4 g | 50 mg | — | 35 mg |

TABLE 3

Composition of paste A in Reference Example 1.

| | Composition of paste A | | | | |
|---|---|---|---|---|---|
| Reference Example | Monomer for radical polymerization (a1) | Insoluble polymer (a2) | Soluble polymer (a3) | Polymerization initiator 2 (a4) | Stabilizer |
| 1 | 20.2 g | 15.5 g | 6.3 g | 2.0 g | 20 mg |

TABLE 4

Composition of paste B in Reference Example 1.

Composition of paste B

| Reference Example | Monomer for radical polymerization (b1) | Soluble polymer (b2) | Insoluble polymer (a2) | Accelerator 2 (b3) | Chloride salt | Colorant | Radio-opacifier | Stabilizer |
|---|---|---|---|---|---|---|---|---|
| 1 | 20.2 g | 11.6 g | 9.8 g | 2 mg | 60 mg | 50 mg | 4.8 g | 35 mg |

The chemicals listed in Table 5 were used for Examples 1-7 and Reference Example 1; the chemicals were procured wholesale at "p.a." purity:

TABLE 5

Components of the Example pastes and Reference Example paste.

| Component according to Tables 1-4 | Chemical |
|---|---|
| Monomer for radical polymerization (a1), (b1): | |
| MMA | Methylmethacrylamide |
| MA | Methacrylamide |
| EGDMA | Ethyleneglycol dimethacrylate |
| Insoluble polymer (a2) | Ethyleneglycol dimethacrylate-crosslinked poly(methylmethacrylate) of sieve fraction <100 μm. |
| Soluble polymer (a3), (b2) | Poly(methylmethacrylate-co-methylacrylate) having a molar mass of <500,000 g/mol |
| Polymerization initiator 1 (a4): | BPO (75%) |
| Polymerization initiator 2 (a4): | 1-Cyclohexyl-5-ethylbarbiturate |
| Stabilizer | 2,6-Di-t-butyl-4-methyl-phenol |
| Accelerator 1 (b3) | N,N-2,2-Bis-hydroxyethyl-p-toluidine (BHET) |
| Accelerator 2 (b3) | Copper(II)-2-ethylhexanoate |
| Colorant | Green aluminum colored lacquer (Sumrise) |
| Antibiotic | Gentamicin sulfate (Fujian Fukang Ltd.) having an activity coefficient of AC = 622 |
| Chloride salt | Aliquat 336 (trioctylmethylammoniumchloride) |
| Radio-opacifier | Zirconium dioxide |

To prepare the individual pastes, first the monomer for radical polymerization (a1) or (b1) and then the corresponding stabilizer were weighed and placed in an inert plastic vessel in each case. Then, the radical polymerization initiator was dissolved in the respective material for producing paste A and the accelerator was dissolved in the respective material for producing paste B, both under stirring and at room temperature. Then all other components were added. The preparations thus obtained were mixed vigorously with each other. This produced pastes that were stored overnight separate from each other until the final stage of swelling had been reached and spreadable pastes had formed.

Subsequently, pastes A and B of the respective Examples and of Reference Example 1 were mixed with each other. The bone cement pastes thus obtained were used to produce strip-shaped test bodies having dimensions of (75 mm×10 mm×3.3 mm) for the determination of bending strength and flexural modulus and cylindrical test bodies (diameter 6 mm, height 12 mm) for the determination of compressive strength. The test bodies were stored for 24 hours at 23° C. Then, the 4-point bending strength, flexural modulus, and compressive strength of the test bodies were determined using a Zwick universal testing device.

The results of the tests of 4-point bending strength, flexural modulus, and compressive strength of the test bodies are shown in Table 6 below:

TABLE 6

4-point flexural strength, flexural modulus, and compressive strength of the test bodies of Examples 1-7 and Reference Example 1.

| Example no. | 4-point flexural strength [MPa] | Flexural modulus [MPa] | Compressive strength [MPa] |
|---|---|---|---|
| 1 | 73.2 ± 1.3 | 2873 ± 39 | 108.5 ± 4.1 |
| 2 | 67.0 ± 3.8 | 2977 ± 67 | 112.8 ± 3.1 |
| 3 | 66.4 ± 3.2 | 2998 ± 75 | 110.0 ± 2.6 |
| 4 | 68.5 ± 3.4 | 2746 ± 156 | 111.1 ± 4.7 |
| 5 | 67.4 ± 2.1 | 2927 ± 56 | 105.8 ± 3.8 |
| 6 | 64.5 ± 2.4 | 2924 ± 57 | 105.5 ± 3.5 |
| 7 | 70.1 ± 1.4 | 2789 ± 17 | 113.3 ± 1.7 |
| Reference Example 1 | 53.1 ± 1.5 | 2167 ± 95 | 79.5 ± 2.9 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A kit for producing bone cement, the kit comprising at least a paste A and a paste B, wherein:
   (a) the paste A contains:
      at least one monomer (a1) for radical polymerization;
      at least one polymer (a2) insoluble in the monomer (a1);
      at least one polymer (a3) soluble in the monomer (a1); and
      at least one radical polymerization initiator (a4);
   wherein a weight ratio of the at least one polymer (a2) insoluble in the monomer (a1) to the at least one polymer (a3) soluble in the monomer (a1) is at least 2 to 1, and wherein an amount of the polymer (a2) insoluble in the monomer (a1) is in a range of 20% to 70% by weight relative to a total weight of paste A; and
   (b) the paste B contains:
      at least one monomer (b1) for radical polymerization;
      at least one polymer (b2) soluble in the monomer (b1);
      at least one accelerator (b3) soluble in the monomer (b1); and
      optionally a polymer (b4) insoluble in the monomer (b1),
   wherein a maximum quantity of the polymer (b4) insoluble in the monomer (b1) is 5% by weight, relative to a total weight of the paste B; and
   wherein a weight ratio of the polymer (b4) insoluble in the monomer (b1) to the at least one polymer (b2) soluble in the monomer (b1) is no more than 0.2;

wherein a fraction of paste A in the kit is 30%-70% by weight and a fraction of paste B in the kit is 30%-70% by weight relative to a total weight of paste A and paste B.

2. The kit according to claim 1, wherein at least one of the monomer (a1) and monomer (b1) for radical polymerization is a methacrylate monomer.

3. The kit according to claim 2, wherein the at least one methacrylate monomer is selected from the group consisting of methylmethacrylate, ethyleneglycol dimethacrylate, and butane-1,4-diol-dimethacrylate.

4. The kit according to claim 1, wherein the at least one polymer (a2) insoluble in the monomer (a1) is a particulate polymer.

5. The kit according to claim 1, wherein the at least one polymer (a2) insoluble in the monomer (a1) is selected from the group consisting of cross-linked polymers.

6. The kit according to claim 1, wherein at least one of the polymer (a3) and the polymer (b2) is selected from the group consisting of poly(methylmethacrylate) copolymers.

7. The kit according to claim 6, wherein the poly(methylmethacrylate) copolymer is selected from the group consisting of poly(methylmethacrylate-co-methylacrylate) and poly(methylmethacrylate-co-styrene).

8. The kit according to claim 1, wherein the paste B contains no insoluble polymer (b4).

9. The kit according to claim 1, wherein the at least one radical polymerization initiator (a4) is selected from the group consisting of (i) peroxides and (ii) barbiturates selected from the group consisting of 1,5-dialkyl-barbiturates, 1-cycloalkyl-5-alkyl-barbiturates and 1-aryl-5-alkyl-barbiturates.

10. The kit according to claim 1, wherein the at least one polymerization accelerator (b3) soluble in monomer (b1) is selected from the group consisting of N,N-dimethyl-p-toluidine, N,N-bis-hydroxyethyl-p-toluidine, N,N-dimethyl-aniline, 4-N,N-dimethylamino-pyridine, saccharin, lithium chloride, trioctylmethylammoniumchloride, organic copper (II) salts, and mixtures thereof.

11. The kit according to claim 1, wherein at least one of the paste A and the paste B contains a radio-opacifier.

12. The kit according to claim 1, wherein at least one of the paste A and the paste B contains at least one pharmaceutical agent.

13. The kit according to claim 1, wherein the kit further comprises:
(i) a first container and a second container, wherein the first container contains the paste A and the second container contains the paste B, and wherein at least one of the first and second containers can be opened to allow the paste A and the paste B to be mixed after opening, and
(ii) a mixing unit for mixing the paste A with the paste B.

14. A method for producing bone cement, the method comprising:
(i) providing a kit for producing bone cement, the kit comprising at least a paste A and a paste B, wherein
(a) the paste A contains:
at least one monomer (a1) for radical polymerization;
at least one polymer (a2) insoluble in the monomer (a1);
at least one polymer (a3) soluble in the monomer (a1); and
at least one radical polymerization initiator (a4);
wherein a weight ratio of the at least one polymer (a2) insoluble in the monomer (a1) to the at least one polymer (a3) soluble in the monomer (a1) is at least 2 to 1, and wherein an amount of the polymer (a2) insoluble in the monomer (a1) is in a range of 20% to 70% by weight relative to a total weight of paste A; and
(b) the paste B contains:
at least one monomer (b1) for radical polymerization;
at least one polymer (b2) soluble in the monomer (b1);
at least one accelerator (b3) soluble in the monomer (b1); and
optionally a polymer (b4) insoluble in the monomer (b1);
wherein a maximum quantity of the polymer (b4) insoluble in the monomer (b1) is 5% by weight, relative to a total weight of the paste B; and
wherein a weight ratio of the polymer (b4) insoluble in the monomer (b1) to the at least one polymer (b2) soluble in the monomer (b1) is no more than 0.2; and
(ii) mixing the paste A and the paste B with each other at a mixing ratio of 0.5-1.5 parts by weight of paste A to 0.5-1.5 parts by weight of paste B.

15. The kit according to claim 1, wherein the paste A contains 15-75% by weight of the at least one monomer (a1) for radical polymerization, 20-70% by weight of the at least one polymer (a2) insoluble in the monomer (a1), 1-25% by weight of the at least one polymer (a3) soluble in the monomer (a1), and 0.00001-15% by weight of the at least one radical polymerization initiator (a4), relative to a total weight of the paste A, and the paste B contains 10-70% by weight of the at least one monomer (b1) for radical polymerization, 20-85% by weight of the at least one polymer (b2) soluble in the monomer (b1), and 0.00001-15% by weight of the at least one accelerator (b3), relative to a total weight of the paste B.

* * * * *